United States Patent
Fischer

(10) Patent No.: US 9,198,607 B2
(45) Date of Patent: Dec. 1, 2015

(54) ARMBAND FOR A DETECTION DEVICE FOR THE DETECTION OF A BLOOD COUNT PARAMETER

(75) Inventor: Georg Fischer, Nuremberg (DE)

(73) Assignees: eesy-id GmbH, Gräfelfing (DE); Friedrich-Alexander-Universitaet Erlangen-Nuernberg, Erlangen (DE)

( * ) Notice: Subject to any disclaimer, the term of this patent is extended or adjusted under 35 U.S.C. 154(b) by 52 days.

(21) Appl. No.: 13/884,367

(22) PCT Filed: Oct. 28, 2011

(86) PCT No.: PCT/EP2011/069033
§ 371 (c)(1),
(2), (4) Date: Jul. 17, 2013

(87) PCT Pub. No.: WO2012/069281
PCT Pub. Date: May 31, 2012

(65) Prior Publication Data
US 2013/0289375 A1    Oct. 31, 2013

(30) Foreign Application Priority Data
Nov. 24, 2010 (EP) .................... 10192472

(51) Int. Cl.
*A61B 5/00* (2006.01)
*A61B 5/145* (2006.01)
*A61B 5/05* (2006.01)
*A61B 5/01* (2006.01)

(52) U.S. Cl.
CPC ............. *A61B 5/145* (2013.01); *A61B 5/0507* (2013.01); *A61B 5/14532* (2013.01); *A61B 5/14546* (2013.01); *A61B 5/681* (2013.01); *A61B 5/6824* (2013.01); *A61B 5/6843* (2013.01); *A61B 5/6886* (2013.01); *A61B 5/01* (2013.01)

(58) Field of Classification Search
CPC ............... A61B 5/145; A61B 5/14532; A61B 5/14546; A61B 5/1455; A61B 5/68; A61B 5/6824; A61B 5/6885
USPC .................. 600/310, 322, 323, 335, 344, 316
See application file for complete search history.

(56) References Cited

U.S. PATENT DOCUMENTS

| | | | | |
|---|---|---|---|---|
| 6,461,305 | B1* | 10/2002 | Schnall | 600/485 |
| 7,164,938 | B2* | 1/2007 | Geddes et al. | 600/324 |
| 8,882,670 | B2* | 11/2014 | Hancock | 600/309 |
| 2005/0256411 | A1 | 11/2005 | Yang | |
| 2012/0016210 | A1 | 1/2012 | Kim et al. | |

FOREIGN PATENT DOCUMENTS

| | | |
|---|---|---|
| DE | 102009011381 A1 | 9/2010 |
| WO | WO-2006089763 A1 | 8/2006 |
| WO | WO-2010118537 A1 | 10/2010 |
| WO | WO-2011128209 A2 | 10/2011 |

OTHER PUBLICATIONS

International Search Report for PCT/EP2011/069033 dated Jan. 30, 2012.

* cited by examiner

*Primary Examiner* — Eric Winakur
(74) *Attorney, Agent, or Firm* — Marshall, Gerstein & Borun LLP

(57) ABSTRACT

An armband comprising a detection device for detecting a blood count parameter in a blood vessel of the arm and an adjustment device for adjusting a predefined contact pressure of the armband on the arm.

19 Claims, 25 Drawing Sheets

ARMBAND FOR A DETECTION DEVICE FOR THE DETECTION OF A BLOOD COUNT PARAMETER

BACKGROUND OF THE INVENTION

1. Field of the Invention

The present invention relates to the field of detecting a concentration of a blood constituent, for example sugar in blood flowing through a blood vessel.

2. Related Technology

In order to ascertain a blood picture parameter, such as, for example, a concentration of a blood constituent, blood can be taken invasively. The blood picture parameter can then be ascertained using the taken blood by means of standardized test strips, the electric resistance values of which depend on the concentration of the blood constituent, e.g. blood sugar. By way of example, the respective electric resistance value can be detected using a blood sugar measuring instrument, which carries out a DC current resistance measurement for detecting an electric resistance value of a test strip. The resistance value can be converted into a blood sugar concentration on the basis of a relationship, known per se, between a blood sugar concentration and a resistance value. In order to obtain high detection accuracy, each test strip is provided with calibration data, for example with a reference resistance value or with a corresponding code, as a result of which variations of properties of the test strips can be compensated for. However, a disadvantage of invasive methods is the necessity of taking blood and hence of injuring a patient. Moreover, continuous detection of a concentration of a blood constituent, for example to establish the diurnal variation curve thereof, is complicated. Furthermore, it is not possible to detect a time delay between food being taken and, for example, an increase in the blood sugar accurately by means of the invasive method. Also, particularly in the case of a low concentration of the blood sugar in blood, the time for administering insulin to the patient cannot be ascertained accurately.

For noninvasive ascertaining of a blood picture parameter such as, for example, a substance concentration or a substance composition in the blood, use can be made of microwave-spectroscopic methods. Microwave spectroscopy for detecting blood picture parameters is based on coupling a microwave signal into tissue perfused by blood and detecting a frequency-dependent absorption of coupled-in microwave energy.

The article "Non-invasive glucose monitoring in patients with Type 1 diabetes: A multi-sensor system combining sensors for dielectric and optical characterization of skin", Biosensors and Bioelectronics 24 (2009) 2778-2784 by Andreas Caduff et al. describes a multi-electrode arrangement for microwave-based ascertaining of a blood picture parameter. The multi-electrode arrangement comprises a plurality of electrode pairs with different electrode spacings, by means of which different penetration depths of microwave signals can be realized. The blood picture parameter is detected by means of an impedance measurement, i.e. by means of a one-port measurement, and is therefore susceptible to errors in the case of possible impedance maladjustments. As a result of different penetration depths, it is sometimes not possible to distinguish between capillary and venous blood, which can falsify the measurement results. In general, a measurement of a blood picture parameter using venous blood is more precise than a measurement of the blood picture parameter using capillary blood because, for example, blood sugar changes in capillary blood are delayed compared to venous blood.

The articles "A microwave frequency sensor for non-invasive blood-glucose measurement", SAS 2008—IEEE Sensors Applications Symposium, Atlanta, Ga., Feb. 12-14, 2008, by Buford Randal Jean et al. and "Calibration methodology for a microwave non-invasive glucose sensor", Master's Thesis, Baylor University, May 2008 by M. McClung describe a further electrode arrangement for ascertaining a blood sugar concentration. What is exploited here is that the dielectric properties of blood depend on a blood sugar content. By pressing a thumb onto the microwave sensor, a change in the relative permittivity of the thumb is measured by a detuning of a resonator. However, blood is displaced by the contact pressure of the thumb, and this can lead to falsification of the measurement results. Moreover, the measurements cannot be carried out continuously. The evaluation of the measurement data for ascertaining the blood sugar content moreover depends on the respective patient and is therefore not reproducible in other patients. Moreover, this method does not allow control of the penetration depth of the microwave power, and so it is not possible to distinguish between capillary and venous blood. Furthermore, the change in the relative permittivity is carried out on the basis of a one-port measurement, which is susceptible in respect of maladjustments.

SUMMARY OF THE INVENTION

The invention provides a reproducible concept for microwave-based, non-invasive ascertaining of a blood picture parameter, in particular of a concentration of blood sugar, in blood flowing through a blood vessel. Accordingly, the invention provides an armband, comprising a detection device for detecting a blood picture parameter of blood in a blood vessel of the arm and a setting device for setting a predetermined contact pressure of the armband on the arm.

The invention further provides a method for operating an armband having a detection device for detecting a blood picture parameter of blood in a blood vessel in the arm, comprising setting a predetermined contact pressure of the armband on the arm.

The invention is based on the discovery that measurements or detections of blood picture parameters by an armband with a detection device can be provided in a reproducible fashion if the armband with the detection device is pressed on the arm with a predetermined or prescribed contact pressure during the measurements. In order to provide the predetermined contact pressure, the armband is additionally equipped with a setting device in addition to the detection device. The setting device is configured in such a way that it can set the predetermined or prescribed contact pressure, at least during the detection of the blood picture parameter by the detection device.

The armband with the detection device and the setting device is configured to be applied to the arm of the patient, particularly in the region of his wrist.

In particular, this location of the wrist does not impair the freedom of movement of the patient. Furthermore, this location is already established for patients for conventional blood pressure measuring instruments. A further advantage in placing the armband on the wrist consists of the fact that the pulse is usually felt at this position, the skin is thin and hence sources of errors can be reduced. Furthermore, by pressing on the armband during the detection of the blood picture parameter, air gaps, which could change a microwave-technical adjustment by the detection device, are avoided. By pressing on the armband with the predetermined contact pressure, the armband can match the anatomy of the respective patient.

By using the armband with the detection device and the setting device, the blood picture parameter can be monitored continuously. An example of such a blood picture parameter is—as explained above—the blood sugar concentration. As a result of the option of continuous monitoring of the blood sugar concentration, determining the delay time between taking up food and the increase in blood sugar is made possible. Furthermore, it is possible to react very quickly to variations in the daily routine of the patient. In particular, an alarm can be triggered in a timely fashion in the case of too much sugar or too little sugar.

In accordance with one aspect of the invention, an armband is proposed, which comprises a detection device for detecting a blood picture parameter of blood in a blood vessel of the arm and a setting device for setting a predetermined contact pressure of the armband on the arm.

In accordance with one embodiment, the setting device is configured to set the contact pressure of the armband to the predetermined contact pressure at least during the detection of the blood picture parameter by the detection device.

In accordance with one embodiment, the setting device comprises a sensor apparatus for measuring a current contact pressure of the armband on the arm and a control apparatus for setting the predetermined contact pressure depending on the measured current contact pressure.

In accordance with one embodiment, the sensor apparatus is arranged on the inner side of the armband.

In accordance with one embodiment, the armband is configured as an inflatable armband.

In accordance with one embodiment, the setting device comprises an air pump which is configured to inflate the armband in order to set the predetermined contact pressure.

In accordance with one embodiment, the setting device comprises a sensor apparatus for measuring a current contact pressure of the armband on the arm, a control apparatus for providing a control signal depending on the measured current contact pressure and an air pump, controlled by means of the provided control signal, for inflating the armband.

In accordance with one embodiment, the detection device comprises electrodes, which are configured to couple at least one radiofrequency signal into the blood vessel.

In accordance with one embodiment, the setting device is configured to set the contact pressure of the electrodes on the arm to the predetermined contact pressure.

In accordance with one embodiment, the setting device is configured to distribute the contact forces of the armband uniformly on the arm during the detection of the blood picture parameter by the detection device.

In accordance with one embodiment, the setting device is configured to provide uniform contact of the armband during the detection of the blood picture parameter by the detection device.

In accordance with one embodiment, the setting device is configured to keep the contact pressure of the armband constant during the detection of the blood picture parameter by the detection device.

In accordance with one embodiment, the armband furthermore comprises a storage medium for providing the predetermined contact pressure.

The predetermined contact pressure stored in the storage medium can advantageously be set. It follows that different contact pressures can be predetermined for different patients.

In accordance with one embodiment, the at least one blood picture parameter comprises a glucose concentration in the blood, a lactate concentration in the blood or an oxygen concentration in the blood.

In accordance with one embodiment, the detection device has a transmitter, a receiver, a loss detector and a processor. The transmitter is configured to couple a first transmission signal with a first frequency and a second transmission signal with a second frequency into the blood vessel. The receiver is configured to receive a first reception signal at the first frequency and a second reception signal at the second frequency. The loss detector is configured to establish a first loss variable on the basis of the first transmission signal and the first reception signal. The loss detector is furthermore configured to establish a second loss variable on the basis of the second transmission signal and the second reception signal. The processor is configured to ascertain a relaxation time constant ($\tau$) of the blood constituent depending on the frequency with the greater loss variable.

In particular, the processor is configured to ascertain the relaxation time constant ($\tau$) of the blood constituent depending on the first frequency if the first loss variable is no smaller than the second loss variable, or to ascertain the relaxation time constant ($\tau$) of the blood constituent depending on the second frequency if the second loss variable is no smaller than the first loss variable.

In accordance with one embodiment, the detection device comprises a transmitter, which is configured to couple a first transmission signal with a first frequency and a second transmission signal with a second frequency into the blood vessel, a receiver, which is configured to receive a first reception signal at the first frequency and a second reception signal at the second frequency, and a loss detector, which is configured to ascertain a first loss variable on the basis of the first transmission signal and the first reception signal at the first frequency and to ascertain a second loss variable on the basis of the second transmission signal and the second reception signal at the second frequency, as well as a processor, which is configured to ascertain a first frequency shift of the first loss variable relative to a first reference loss variable, to ascertain a second frequency shift of the second loss variable relative to a second reference loss variable, and to ascertain the blood picture parameter on the basis of the first frequency shift and the second frequency shift.

By way of example, the first reference loss variable and the second reference loss variable can be ascertained in advance on the basis of experiments or measurements. By way of example, if the first loss variable and the second loss variable are absorption lines, the first reference loss variable and the second reference loss variable can, for example, be absorption lines of a reference water solution with a predetermined concentration of a blood constituent, e.g. blood sugar.

In accordance with one embodiment, the invention relates to a detection device for detecting a blood picture parameter of blood in a blood vessel, comprising a transmitter with a number of transmission antennas for emitting at least one transmission signal, a receiver with a number of reception antennas for receiving at least one reception signal, a processor, which is configured to select a first detection configuration comprising one transmission antenna of the number of transmission antennas and one reception antenna of the number of reception antennas and to select a second detection configuration comprising one transmission antenna of the number of transmission antennas and one reception antenna of the number of reception antennas, a loss detector, which is configured, if the first detection configuration for emitting a transmission signal is selected, to detect a first loss variable on the basis of the transmission signal and a reception signal and, if the second detection configuration for emitting a transmission signal is selected, to detect a second loss variable on the basis of the transmission signal and a reception signal, wherein the processor is configured to select the detection configuration with the smaller loss variable for detecting the blood picture parameter.

During the selection of the respective detection configuration, it is preferable for the blood vessel to be excited, wherein the transmission signals are, for example, emitted in the direction of the blood vessel. On the basis of the reception signals, which are received versions of the transmission signals, and on the basis of the transmission signals it is possible, for example, to select that antenna pair, comprising a transmission antenna and a reception antenna, as that detection configuration which is connected with the smallest coupling-in losses. The coupling-in losses can, for example, be detected on the basis of a comparison of the aforementioned loss variables, for example absorption lines or attenuations.

In accordance with one aspect of the invention, a method for operating an armband having a detection device for detecting a blood picture parameter of blood in a blood vessel in the arm is proposed, in which a predetermined contact pressure of the armband on the arm is set.

BRIEF DESCRIPTION OF THE DRAWINGS

Further exemplary embodiments will be explained in more detail with reference to the attached drawings. In detail.

DETAILED DESCRIPTION

Figure 1:
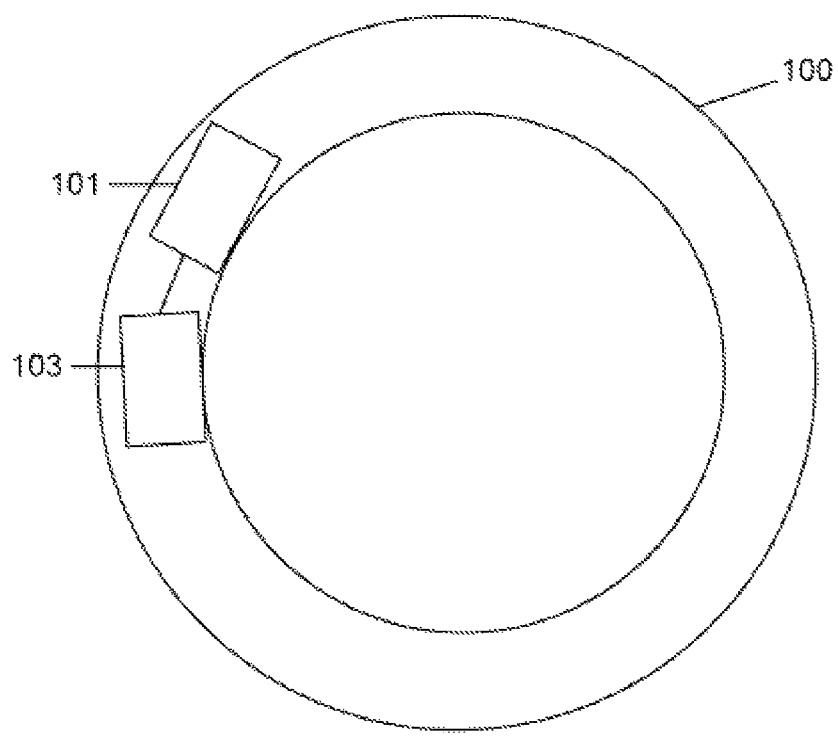
FIG. 1 shows a schematic block diagram of an armband.

FIG. 1 shows a block diagram of an exemplary embodiment of an armband 100 with a detection device 101 and a setting device 103. The detection device 101 is configured to detect a blood picture parameter of blood in a blood vessel of the arm. An example for the blood picture parameter to be detected is the glucose concentration in the blood.

The setting device 103 is configured to set a predeterminable contact pressure of the armband 100 on the arm. By setting the predetermined contact pressure of the armband 100, the setting device 103 can ensure reproducible detections of the blood picture parameter by the detection device 101. To this end, the setting device 103 is, in particular, configured to set the contact pressure of the armband 100 to the predeterminable contact pressure when the blood picture parameter is being detected by the detection device 101.

In particular, the armband 100 is embodied as an inflatable armband 100. Here, the setting device 103 in particular has an air pump, which is configured to inflate the armband 100 for setting the predetermined contact pressure.

In detail, the detection device 101 comprises electrodes in particular, which are configured to couple at least a radiofrequency signal into the blood vessel. The radiofrequency signal is configured to supply a parameter for detecting the blood picture parameter. An example for such a parameter is formed by the relaxation time constant $\tau$ of the blood picture parameter. Here, the setting device 103 is more particularly designed to set the contact pressure of the electrodes on the arm to the predetermined contact pressure.

Furthermore, the setting device 103 can be embodied in such a way that it distributes the contact forces of the armband 100 uniformly on the arm when the blood picture parameter is being detected by the detection device 101. Furthermore, the setting device 103 is preferably configured in such a way that it ensures uniform contact of the armband 100 while the blood picture parameter is being detected by the detection device 101.

Figure 2:
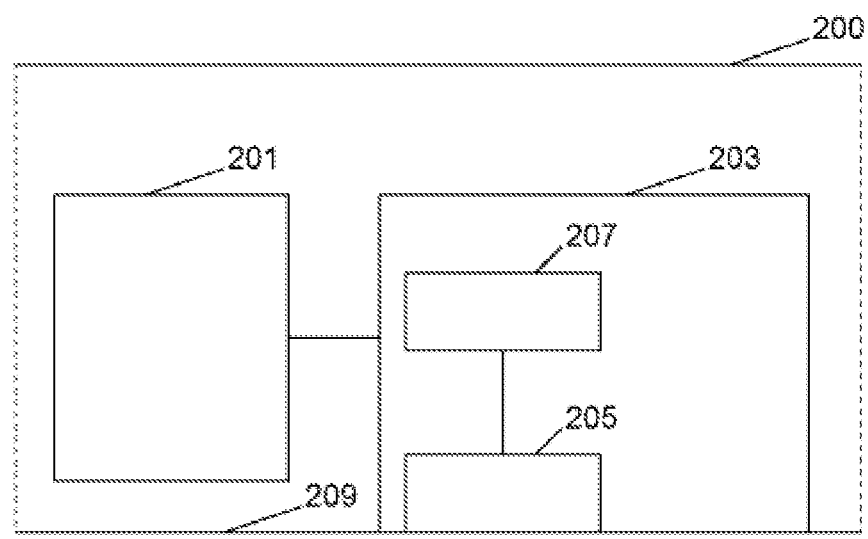
FIG. 2 shows a schematic block diagram of a section of an armband.

FIG. 2 shows a block diagram of a section of an exemplary embodiment of an armband 200. The armband 200 has a detection device 201 and a setting device 203. The detection device 201 and the setting device 203 are embodied at least like the detection device 101 and the setting device 103 of FIG. 1. Furthermore, the setting device 203 of FIG. 2 has a sensor apparatus 205 and a control apparatus 207. The sensor apparatus 205 is configured to measure a current contact pressure of the armband 200 on the arm. Depending on the measured current contact pressure, the control apparatus 207 sets the predetermined contact pressure on the arm.

Figure 3:
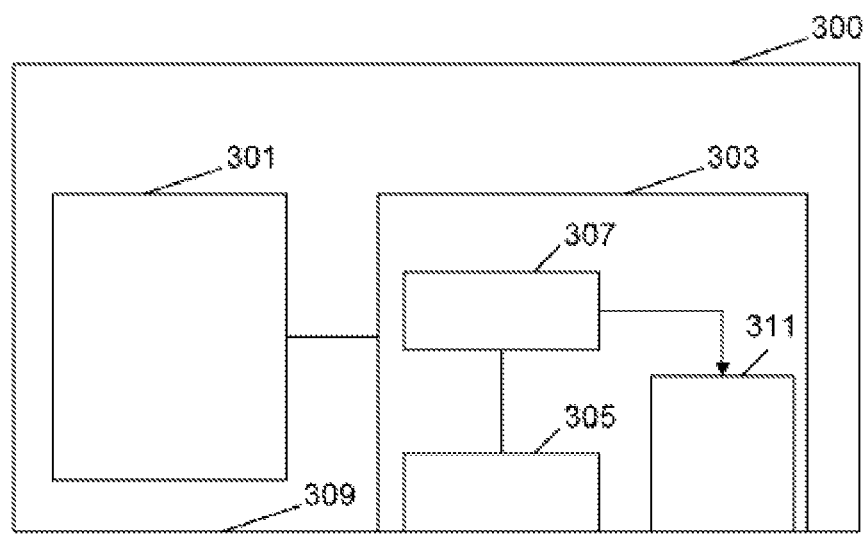
FIG. 3 shows a schematic block diagram of a section of an armband.

FIG. 3 shows a block diagram of a section of a further exemplary embodiment of an armband 300. The armband 300 has a detection device 301 and a setting device 303. The setting device 303 has a sensor apparatus 305, a control apparatus 307 and an air pump 311. The sensor apparatus 305 measures a current contact pressure of the armband 300 on the arm. The control apparatus 307 provides a control signal depending on the measured current contact pressure. By means of the provided control signal, the air pump 311 is controlled for inflating the armband 300.

Figure 4:
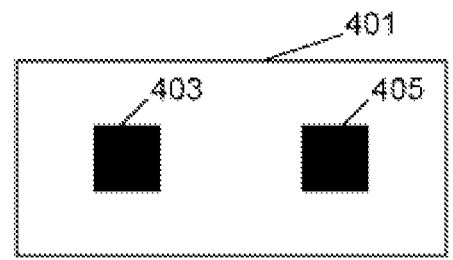
FIG. 4 shows a schematic block diagram of an arrangement of the electrodes of the detection device.

FIG. 4 illustrates a schematic block diagram of an arrangement 400 of the electrodes 403, 405 of the detection device for detecting a blood picture parameter of blood in a blood vessel of the arm.

Without loss of generality, the arrangement 400 only shows two electrodes 403 and 405. In particular, the arrangement 400 is part of the detection device and, for example, embodied as a plate with exemplary dimensions of 5 cm by 2 cm. The electrodes 403, 405 for example have a base area of 5 mm by 5 mm. By way of example, the distance between the electrodes 403, 405 is 1 to 2 cm. This firstly obtains a strong enough transmission and secondly ensures a sufficiently deep penetration depth into the body.

Figure 5:
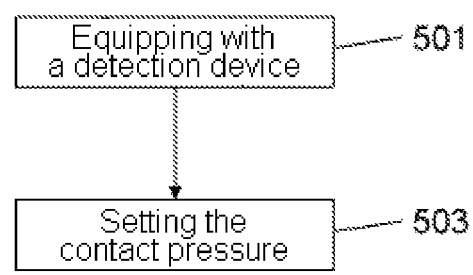
FIG. 5 shows a schematic flowchart of a method for operating an armband.

FIG. 5 shows a schematic flowchart of a method for operating an armband with a detection device.

In step 501, the armband is equipped with a detection device for detecting a blood picture parameter of blood in a blood vessel of the arm. By way of example, the detection device is configured in accordance with one of the exemplary embodiments of FIG. 1, 2 or 3.

In step 503, a predetermined contact pressure of the armband on the arm is set. Hence, reproducible detection of the blood picture parameter is ensured by the detection device.

Figure 6:
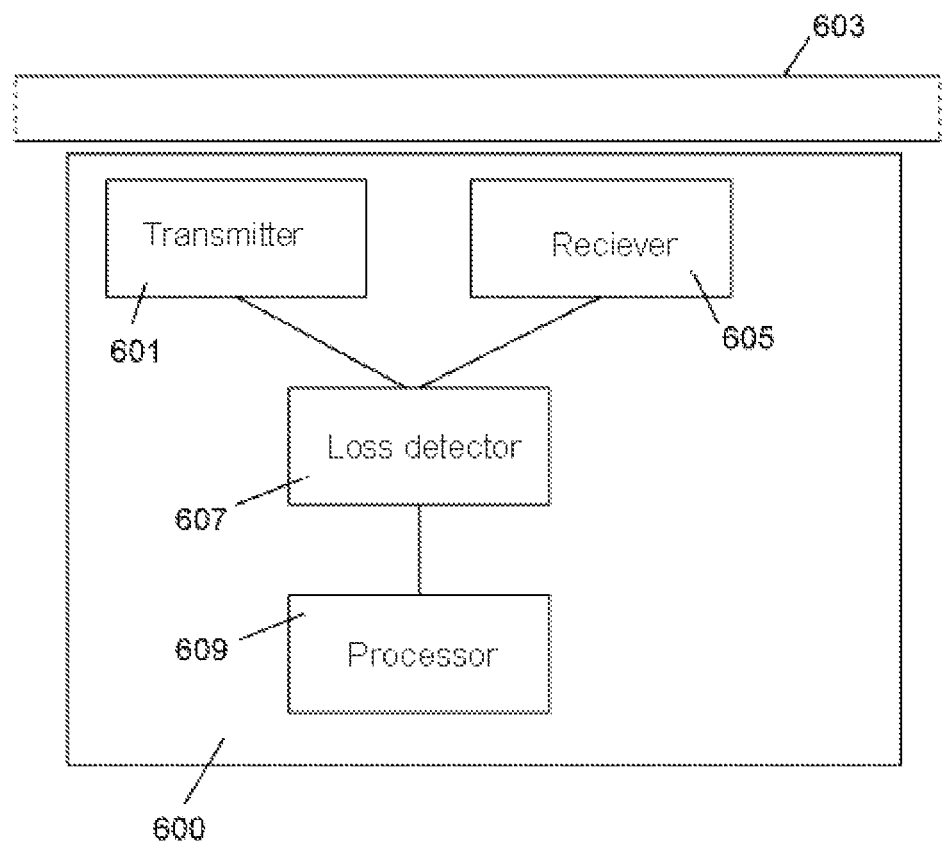
FIG. 6 shows a schematic block diagram of an exemplary embodiment of a detection device.

FIG. 6 shows a block diagram of a detection device 600 for detecting a blood picture parameter, such as, for example, a concentration of blood sugar or glucose. The detection device 600 comprises a transmitter 601, which is configured to couple a first transmission signal with a first frequency and a second transmission signal with a second frequency into the blood vessel 603 illustrated schematically in FIG. 6. The first transmission signal and the second transmission signal can, for example, together result in a broadband signal. The transmitter 601 can furthermore be configured to couple the first transmission signal and the second transmission signal, one after the other, into the blood vessel 603 in sequence. To this end, the transmitter 601 can have one or more transmission antennas, which, for example, are formed as dipole antennas.

The detection device 600 furthermore comprises a receiver 605, which is configured to receive a first reception signal at the first frequency and a second reception signal at the second frequency. To this end, the receiver 605 can have one or more reception antennas.

Furthermore, the detection device 600 has a loss detector 607, which is, for example, coupled to the transmitter 601 and the receiver 605 and provided for ascertaining a first loss variable on the basis of the first transmission signal and the first reception signal and also a second loss variable the basis of the second transmission signal and the second reception signal.

The detection device 600 furthermore has a processor 609, which is coupled to the loss detector 607 and provided for ascertaining a relaxation time constant τ of the blood picture parameter depending on the frequency with the greater loss variable.

By way of example, the processor 609 will ascertain the relaxation time constant of the blood picture parameter depending on the first frequency if the first loss variable is greater than the second loss variable. Correspondingly, the processor 609 will ascertain the relaxation time constant (τ) of the blood picture parameter depending on the second frequency if the second loss variable is greater than the first loss variable.

The detection device 600 illustrated in FIG. 6 uses the discovery that a blood vessel such as e.g. a vein, a layer of skin and fatty tissues surrounding a vein can be considered to be a dielectric waveguide. The makeup of a human forearm is described in Netter, F. N. "Atlas der Anatomie" [Anatomical Atlas], Thieme Verlag, 2006. Accordingly, a human forearm in cross-section consists of two bones which are surrounded by muscular tissue. Distributed around the muscular tissue are surface veins. The bones, the muscular tissue and the veins are encapsulated by fatty tissue, which is covered by upper layers of skin. The surface veins are arranged relatively close to the upper layers of skin and separated therefrom by the fatty tissue.

By way of example, if the transmitter 601 and the receiver 605, illustrated in FIG. 6, are placed onto the upper layer of skin, the transmitter 601 can be used to couple a transverse electric (TE) wave or a transverse magnetic (TM) wave into the dielectric waveguide system formed by a vein, fatty tissue and a layer of skin. Here, the layer of skin and the fatty tissue can be understood to be a thin-film waveguide.

As already explained above, the loss detector 607 is configured to establish a first loss variable on the basis of the first transmission signal and the first reception signal and to establish a second loss variable on the basis of the second transmission signal and the second reception signal. If use is made of further transmission signal and reception signal pairs, the loss detector 607 will accordingly establish further loss variables.

In particular, the loss detector 607 is configured to ascertain the loss variables by a two-port measurement. By way of example, the loss detector 607 comprises a network analyzer or a power detector.

Furthermore, the loss detector 607 is configured to ascertain in each case a forward transmission factor $S_{21}$ and an input reflection factor $S_{11}$ in order to ascertain the loss variables.

Here, the loss detector will calculate the respective loss variable $P_{loss}$ by means of the following formula:

$$P_{loss} = 1 - |S_{11}|^2 - |S_{21}|^2.$$

In particular, the loss detector 607 is configured to establish the complex relative permittivity $\in''$ for ascertaining the respective loss variable.

Figure 7:
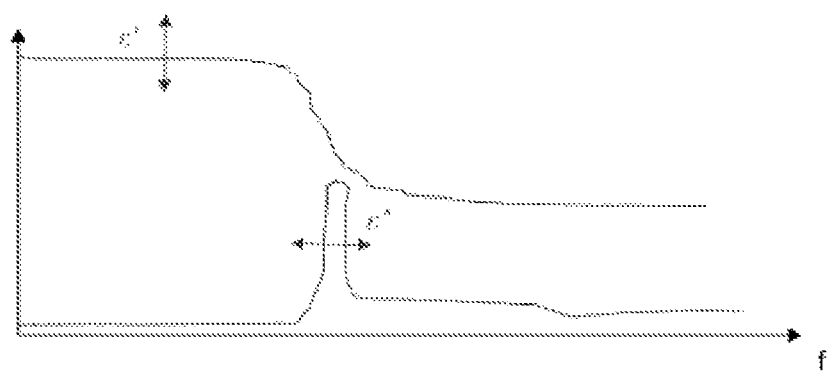
FIG. 7 shows a diagram for illustrating the real relative permittivity $\in'$ and the complex relative permittivity $\in''$ depending on the frequency.

To this end, FIG. 7 shows a diagram for illustrating the real relative permittivity $\in'$ and the complex relative permittivity $\in''$ depending on the frequency f.

Here, FIG. 7 illustrates that the losses represented by the complex relative permittivity $\in''$ increase in the frequency range where the real part $\in'$ transitions from the higher level to the lower level. This increase in the losses is also referred to as absorption lines in spectroscopy. The effect that can be used in this case is that the frequency at which the excesses of the losses—see local maximum of $\in''$—is displaced with the concentration of the sugar content.

By way of example, the human body consists of 80% water. Water has absorption lines, for example at 19 GHz and 50 GHz. The detuning thereof can be ascertained and plotted against the sugar content. The detuning of the resonant frequency at $\in''$ is—as illustrated in FIG. 7—easier to detect than the change in the plateau of $\in'$. In particular, variations in the coupling advantageously do not shift the frequency of the maximum of $\in''$. As a result, ascertaining the sugar concentration by observing $\in''$ is significantly less susceptible to errors than observing $\in'$ or the level change therein.

Since such curves as are superimposed in FIG. 7 in a multiplicity of substances, a separation of the substances by observing the imaginary relative permittivity $\in''$ is easier to carry out since each substance can be associated with a specific absorption maximum. However, in the case of the real relative permittivity $\in'$, it is only possible to observe the sum of all real relative permittivities $\in'$ of all substances involved.

As already explained above, the processor 609 is configured to ascertain the relaxation time constant τ of the blood picture parameter depending on the frequency with the larger or maximum loss variable. Furthermore, the processor 609 is configured to establish the blood picture parameter, such as the glucose concentration in the blood, depending on the ascertained relaxation time constants.

Figure 8:
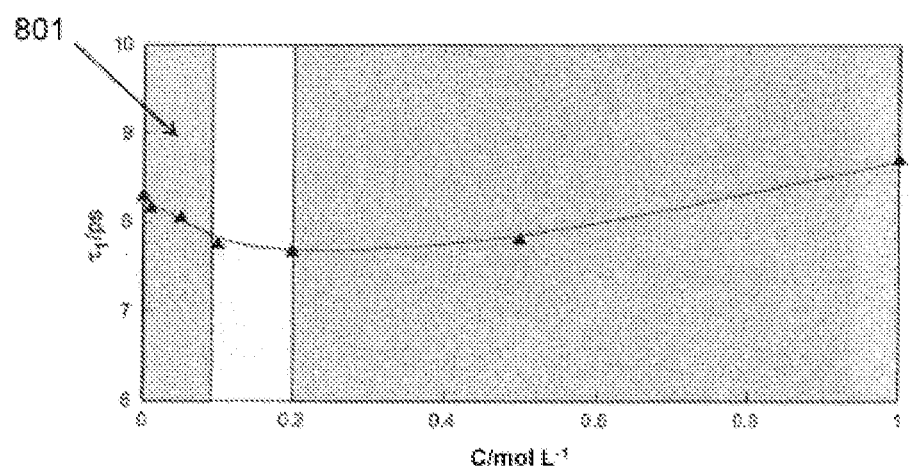
FIG. 8 shows a diagram for illustrating a relationship between the relaxation time constant ($\tau$) and the glucose concentration in the blood.

To this end, FIG. 8 shows a diagram for illustrating a relationship between the relaxation time constant (τ) and the glucose concentration C/mol L⁻¹ in the blood. Here, the area denoted by the reference sign 801 in FIG. 8 shows a critical blood sugar range.

Furthermore, the processor 609 is, in particular, configured to calculate the relaxation time constant (τ) on the basis of the formula $$\tau = \frac{1}{2\pi f_A},$$

where $f_A$ denotes the frequency at which the established loss variable is at a maximum.

Advantageously, the processor 609 is then configured to ascertain the frequency at which the imaginary part of the complex relative permittivity ∈" is at a maximum, and at which the relaxation time constant (τ) is to be established depending on the ascertained frequency. This ascertained frequency is then used by the processor 609 for ascertaining the blood picture parameter, such as the glucose concentration.

Figure 9:
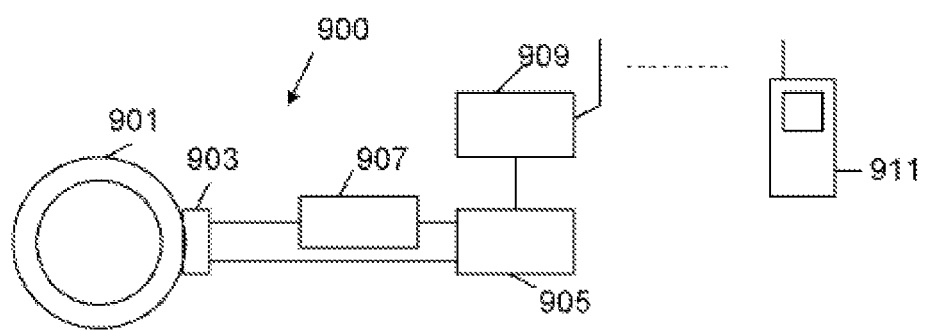
FIG. 9 shows a schematic block diagram of an exemplary embodiment of a detection device with a communication device.

FIG. 9 shows a schematic block diagram of a detection device 900. The detection device 900 has an armband 901, a sensor array 903 attached to the armband 901, a microprocessor 905, a microwave circuit 907 for generating the transmission signals, and a communication device 909.

By way of example, the sensor array 903 has a microwave sensor, a temperature sensor and a moisture sensor.

By way of example, the microprocessor 905 is configured like the processor 609 in FIG. 6.

The communication device 909 is configured for providing a communication link between the detection device 900 and a further communication device 911. By way of example, the communication device 909 comprises a Bluetooth interface. By way of example, the further communication device 911 is a mobile radio device, a smartphone or a GPS-based apparatus.

Figure 10:
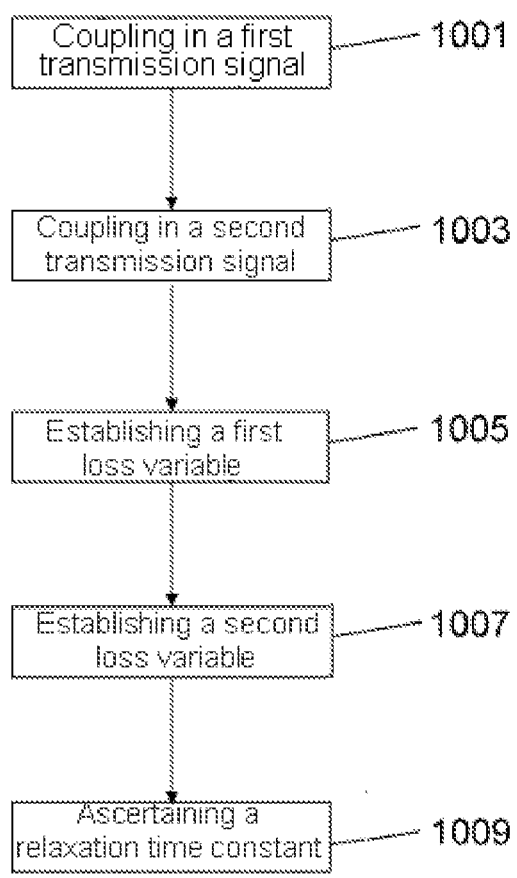
FIG. 10 shows a schematic flowchart of an exemplary embodiment of a method for detecting a blood picture parameter of blood in a blood vessel.

FIG. 10 illustrates a schematic flowchart of an exemplary embodiment of a method for detecting a blood picture parameter, such as, for example, a glucose concentration, of blood in a blood vessel.

In step 1001, a first transmission signal with a first frequency and a second transmission signal with a second frequency are coupled into the blood vessel.

In step 1003, a first reception signal is received at the first frequency and a second reception signal is received at the second frequency.

In step 1005, a first loss variable is established on the basis of the first transmission signal and the first reception signal.

In step 1007, a second loss variable is established on the basis of the second transmission signal and the second reception signal.

In step 1009, a relaxation time constant of the blood picture parameter is ascertained depending on the frequency with a greater loss variable. The glucose concentration in the blood, for example, can then be ascertained depending on the ascertained relaxation time constant.

Figure 11:
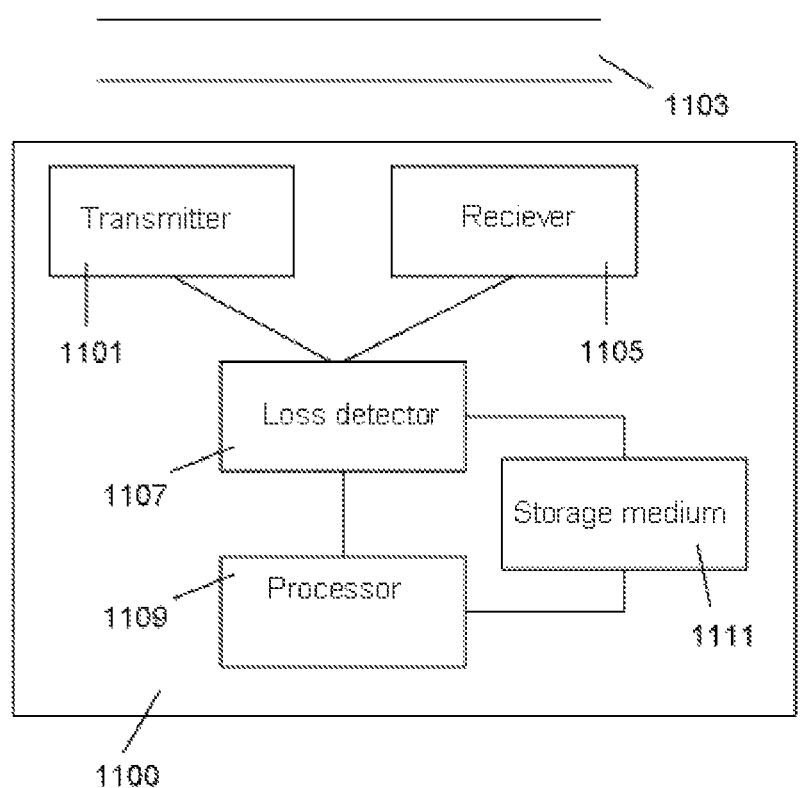
FIG. 11 shows a block diagram of a detection device.

FIG. 11 shows a block diagram of a detection device 1100 for detecting a blood picture parameter such as, for example, a concentration of blood sugar. The detection device 1100 comprises a transmitter 1101, which is configured to couple a first transmission signal with a first frequency and a second transmission signal with a second frequency into the blood vessel 1103 illustrated schematically in FIG. 11. By way of example, together, the first transmission signal and the second transmission signal can result in a broadband signal. The transmitter 1101 can be configured to emit, one after the other, the first transmission signal and the second transmission signal, for example by a frequency sweep. To this end, the transmitter 1101 can have one or more transmission antennas, which can, for example, be embodied as dipole antennas or frame antennas or patch antennas.

The detection device 1100 furthermore comprises a receiver 1105, which is configured to receive a first reception signal at the first frequency and a second reception signal at the second frequency. To this end, the receiver 1105 can have one or more reception antennas.

The detection device 1100 furthermore comprises a loss detector 1107, which, for example, is coupled to the transmitter 1101 and the receiver 1105 and is provided for ascertaining a first loss variable on the basis of the first transmission signal and the first reception signal and also a second loss variable on the basis of the second transmission signal and the second reception signal.

The detection device furthermore comprises a processor 1109, which is coupled to the loss detector 1107 and is provided for ascertaining a first frequency shift of the first loss variable relative to a first reference loss variable and a second frequency shift of the second loss variable relative to a second reference loss variable. The processor 1109 can furthermore be configured to ascertain the blood picture parameter on the basis of the two frequency shifts.

The detection device 1100 can furthermore have a storage medium 1111, which can be accessed by, for example, the processor 1109 and, optionally, the loss detector 1107. By way of example, the first and the second reference loss variable or a plurality of reference loss variables are stored in the storage medium 1111. By way of example, the reference loss variables can be absorptions or absorption lines of a water solution with a blood constituent, for example blood sugar. The loss variables detected on the basis of the frequency shifts can be frequency-shifted absorptions or absorption lines such that the blood picture parameter, such as, for example, a concentration of blood sugar, can be established on the basis of the frequency shifts.

The detection device 1100 illustrated in FIG. 11 uses the discovery that a blood vessel, a layer of skin and fatty tissue surrounding the blood vessel of, for example, a human forearm can be considered to be a dielectric waveguide system. By way of example, if the transmitter 1101 and the receiver 1105, illustrated in FIG. 11, are placed onto the upper layer of skin, the transmitter 1101 can be used to couple e.g. a transverse electric (TE) wave or a transverse magnetic (TM) wave into the dielectric waveguide system formed by a blood vessel, fatty tissue and a layer of skin. Here, the layer of skin and the fatty tissue can be understood to be a thin-film waveguide.

By way of example, if use is made of a microwave measurement head, as can be employed for ascertaining a complex relative permittivity of materials, it is possible thereby to characterize the substance mixture consisting of skin, fatty tissue and veins.

In order to detect a blood picture parameter, it is advantageous to detect substantially only the venous blood. To this end, the transmitter 1101 can be configured to couple the transmission signal in the form of an electromagnetic wave directly into the blood vessel. The transmitter 1101 and the receiver 1105 can each have a plurality of antennas such that, for the purposes of coupling the electromagnetic wave into the blood vessel and decoupling an electromagnetic wave from the blood vessel, it is in each case possible to select that transmission antenna and reception antenna which are connected with the smallest coupling losses.

Figures 12A, 12B, 12C:
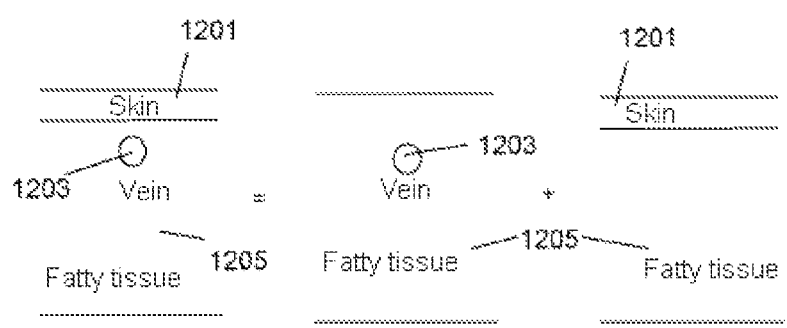
FIG. 12 shows a model of a cross-section of a human forearm.

FIGS. 12A to 12C illustrate a simplified model of a cross-section of a human forearm, e.g. of a wrist, as can be employed, for example, for field simulations or for modeling a dielectric waveguide system. As illustrated in FIG. 12A, the model comprises a layer of skin 1201, a blood vessel 1203 and fatty tissue 1205 surrounding the blood vessel 1203. The model illustrated in FIG. 12A forms a dielectric waveguide system comprising the dielectric waveguide illustrated in FIG. 12B and the electrical thin-film waveguide illustrated in FIG. 12C.

The dielectric waveguide illustrated in FIG. 12B comprises the blood vessel 1203 and the fatty tissue 1205 surrounding the latter. By contrast, the dielectric thin-film waveguide from FIG. 12C comprises the layer of skin 1201 and the fatty tissue 1205. A different dispersive, i.e. frequency dependent, behavior of the respective complex relative permittivity can be attached in each case to the layer of skin 1201, to the fatty tissue 1205 and to the blood vessel 1203. Here, the blood vessel 1203 lying at the top is interpreted as a dielectric waveguide, in which, depending on the frequency, different modes or wave types, for example a TE wave, a TM wave, a TEM wave or an HE wave, are able to propagate. Added to the waveguide mechanism in the dielectric waveguide, there is an additional waveguide mechanism in the form of the thin-film waveguide illustrated in FIG. 12C, which is formed by the upper layer of skin 1201.

A transmission antenna of the transmitter 1101 and a reception antenna of the receiver 1105 can preferably be configured in such a way that they couple microwave power into the blood vessel 1203 in a dedicated fashion and decouple said microwave power again after, for example, a few centimeters. Here, the blood vessel 1203 serves as a measurement length and should therefore be considered as a distributed element and no longer as a concentrated element. The measurement of the loss variables is preferably carried out on the basis of a two-port measurement. Here, particularly when coupling the detection device to a wrist, primary modes can be excited in the dielectric waveguide in accordance with FIG. 12B such that an excitation of thin-film waveguide modes in the thin-film waveguide in accordance with FIG. 12C is avoided, as a result of which the blood picture parameter can be detected more accurately.

In order to excite primary modes in the dielectric waveguide system, it is possible to take into account that, depending on the selected frequency of a transmission signal, different modes can be dominant. It is preferable for mode types, which have a concentration of the fields in the vein 1203, to be preferred over those modes in which the fields are concentrated in the layer of skin 1201. What is shown on the basis of the dielectric properties of the dielectric waveguide illustrated in FIG. 12B is that for certain types of modes longitudinal components $E_{longitudinal}$, $H_{longitudinal}$ are stronger in the propagation direction, i.e. in the direction of a vein extent, than the transverse components $E_{transverse}$, $H_{transverse}$, i.e. transverse to the vein extent. Therefore those modes which enable maximum coupling of the microwave power into the blood vessel 1203 are preferably excited in the frequency range to be detected.

FIGS. 13A to 13D illustrate some antennas in an exemplary fashion, which antennas can be used as transmission antennas, i.e. excitation means, or else as reception antennas.

Figure 13A:
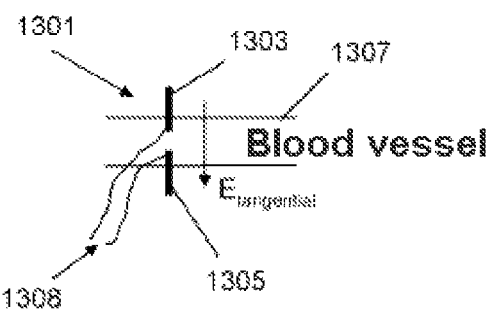
FIGS. 13A-13D show antennas.

The antenna 1301 illustrated in FIG. 13A is configured as an electric dipole with a first antenna section 1303 and a second antenna section 1305. The antenna sections 1303 and 1305 are distanced from one another and are arranged, for example, transversely with respect to the extent of a blood vessel 1307. The antenna 1301 can be excited by supply lines 1308. An electric dipole arranged in this manner can, for example, generate an electric field $E_{tangential}$, which points across the extent of the blood vessel or across the blood flow direction.

Figure 13B:
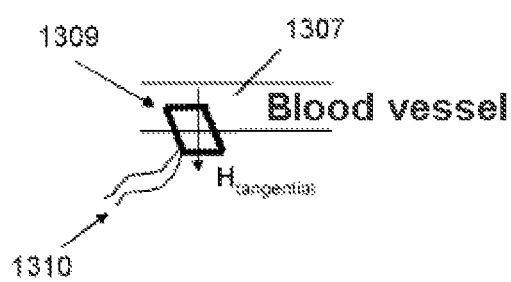

FIG. 13B illustrates an antenna 1309, which can be a frame antenna. By way of example, the frame antenna can have a quadrilateral or round shape. In the arrangement of the frame antenna 1309 with respect to the blood vessel 1307 illustrated in FIG. 13B, e.g. a magnetic field $H_{tangential}$ is excited, which points across the extent of the blood vessel 1307 or across the blood flow direction. The antenna 1309 can be excited by supply lines 1310.

Figure 13C:
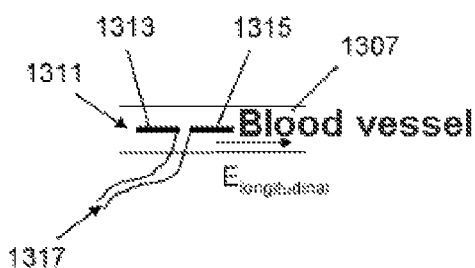

FIG. 13C illustrates an antenna 1311, which forms an electric dipole with a first antenna section 1313 and a second antenna section 1315. The antenna sections 1313 and 1315 are distanced from one another and are excited by means of the supply lines 1317 illustrated in FIG. 13C. The electric dipole formed by the antenna 1311 is arranged in such a way with respect to the extent of the blood vessel 1307 that the sections 1313 and 1315 are arranged parallel to the extent of the blood vessel 1307. As a result of this, an electric field with the field component $E_{longitudinal}$, which electric field points in the direction of the extent of the blood vessel, is excited.

Figure 13D:
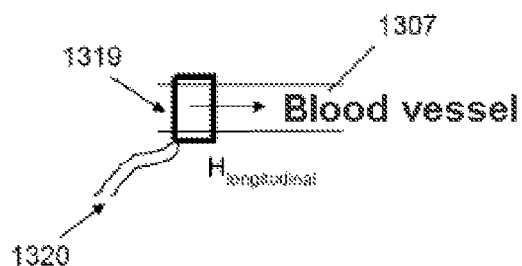

FIG. 13D shows a frame antenna 1319, which can, for example, be formed in the form of a quadrilateral or round frame, which forms a loop antenna, for example as a patch antenna. The frame antenna 1319 is excited by means of supply lines 1320 and is, as illustrated in FIG. 13D, arranged in such a way with respect to the extent of the blood vessel 1307 or with respect to the blood flow direction that the magnetic field has a component $H_{longitudinal}$ pointing in the direction of the extent of the blood vessel 1307.

By way of example, the frequency range to be measured in each case conforms to which spectral lines, i.e. which absorption lines, should be detected. By way of example, it is possible to observe the characteristic absorption lines of a substance or else an effect which a specific blood constituent has on the absorption lines of water or of a water solution with a concentration of the blood constituent.

The antennas illustrated in FIGS. 13A to 13D are either electric dipoles or magnetic frame antennas. Moreover, use can also be made of patch antennas. Electric dipoles dominantly produce an electric field along the axis of the electric dipole. This axis can either, as illustrated in FIG. 13A, be aligned tangentially with respect to the blood vessel 1307 or the blood flow direction or, as illustrated in FIG. 13C, be aligned in the direction of the blood vessel 1307 or in the blood flow direction. If it is primarily a magnetic field that should be generated, a frame antenna can be used as excitation means. If a surface vector on the surface spanned by the frame forming the frame antenna is aligned across the blood vessel 1307 or across the blood flow direction, the magnetic field is also aligned across the blood vessel 1307, as illustrated in FIG. 13B. By contrast, if the surface vector points in the direction of the blood vessel 1307, the magnetic field is also aligned in the direction of the blood vessel 1307, as is illustrated in, for example, FIG. 13B. The selection of an excitation means illustrated in FIGS. 13A to 13D then results in, for example, the dominant excited mode or wave type.

Figure 14A:
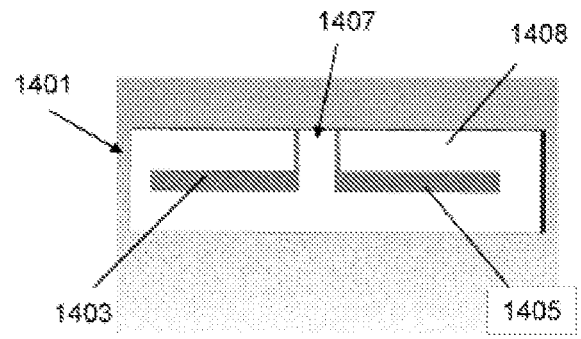
FIG. 14A shows an electric dipole antenna.

FIG. 14A shows an electric dipole antenna 1401, which can be used as a transmission antenna or as a reception antenna. The electric dipole antenna 1401 comprises dipole antenna sections 1403 and 1405, which are arranged in or on a substrate 1408 and can be excited by means of supply lines 1407.

The dipole antenna 1401 can be used as a transmission antenna or as a reception antenna.

Figure 14B:
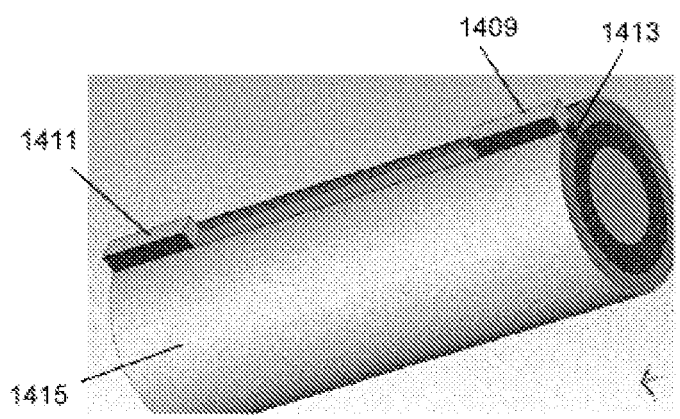
FIG. 14B shows an excitation arrangement.

FIG. 14B shows an excitation arrangement of a transmission antenna 1409 of a transmitter and of a reception antenna 1411 of a receiver in the direction of an extent of a blood vessel 1413 below a layer of skin 1415. The transmission antenna 1409 and the reception antenna 1411 are, for example, electric dipole antennas in accordance with FIG. 14A. In the arrangement illustrated in FIG. 14B, an electric field with a field component in the direction of the extent of the blood vessel 1413, or in the blood flow direction, is generated.

Figure 15A:
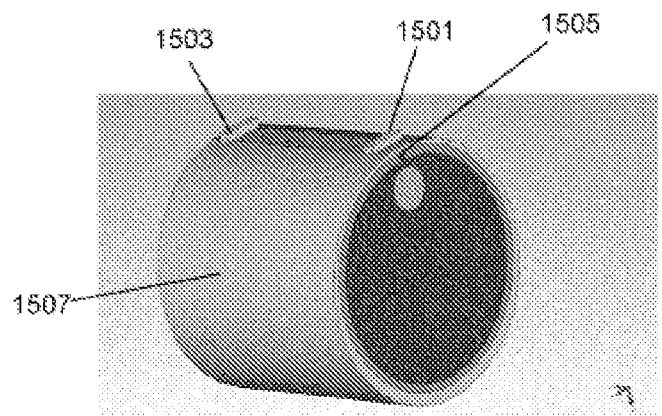
FIGS. 15A, 15B show excitation arrangements.
Figure 15B:
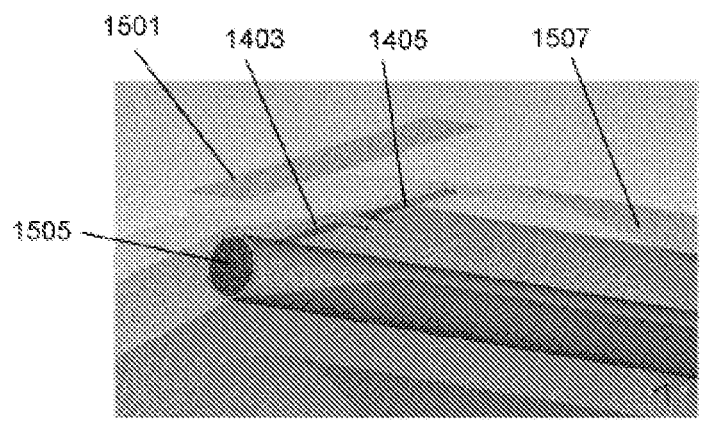

FIG. 15A shows an excitation arrangement comprising a transmission antenna 1501 of a transmitter and a reception antenna 1503 of a receiver, across the direction of extent of a blood vessel 1505, i.e. across the blood flow direction, which lies under a layer of skin 1507. The transmission antenna 1501 and the reception antenna 1503 can each be formed by e.g. the electric dipole antenna illustrated in FIG. 14A. In FIG. 15B, the arrangement of the dipole antenna sections 1403 and 1405 is illustrated in more detail in respect of the blood flow direction.

Figure 16A:
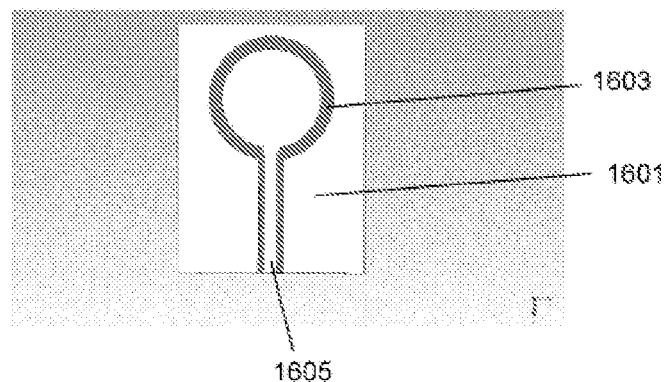
FIG. 16A shows a loop antenna.

FIG. 16A shows a loop antenna 1601 with a circular frame 1603 and supply lines 1605 for exciting the circular frame 1603. The loop antenna 1601 can, for example, be used as a transmission antenna or as a reception antenna. The circular frame 1603 and the supply lines 1605 can be arranged in or on a substrate.

Figure 16B:
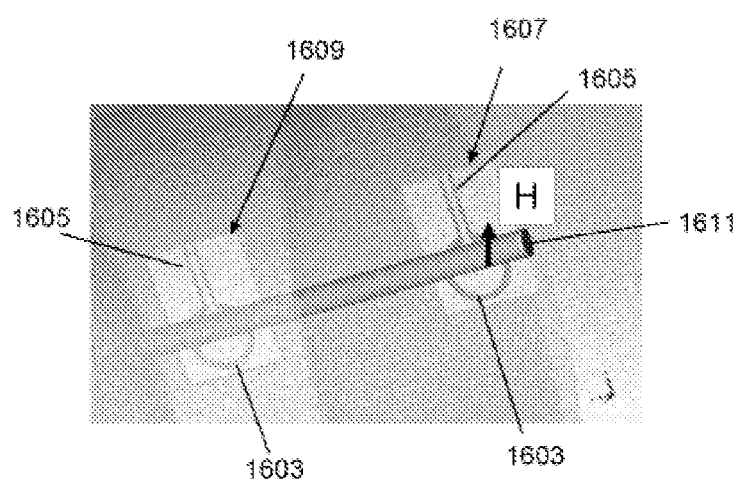
FIG. 16B shows an excitation arrangement.

FIG. 16B shows an excitation arrangement with a transmission antenna 1607 of a transmitter and a reception antenna 1609 of a receiver, which can be formed as loop antennas as per FIG. 16A. By way of example, the loop antennas 1607, 1609 are arranged in such a way that the circular frames 1603 are arranged above a blood vessel 1611, with the supply lines 1605 pointing across the extent of the blood vessel 1611, i.e. across the blood flow direction. As a result of this, a magnetic field H with a component of the magnetic field pointing across the extent of the blood vessel 1611 is generated on the transmitter side.

Figure 17:
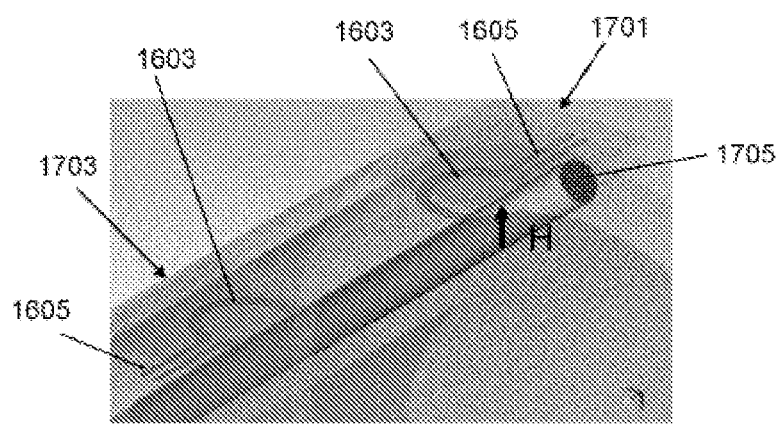
FIG. 17 shows an excitation arrangement.

FIG. 17 shows an excitation arrangement of a transmission antenna 1701 of a transmitter and a reception antenna 1703 of a receiver, with respect to a blood vessel 1705. By way of example, the transmission antenna 1701 and the reception antenna 1703 can be loop antennas with that shape illustrated in FIG. 16A. By way of example, they are arranged in such a way that the circular frames 1603 are respectively arranged above the blood vessel 1705 and that the supply lines 1605 extend pointing away from one another, parallel to the extent of the blood vessel 1705. As a result of this, a field component H pointing perpendicular to the extent of the blood vessel 1705 is generated, which field component points in the direction of a normal of the surface spanned by the circular frame 1603.

Figure 18:
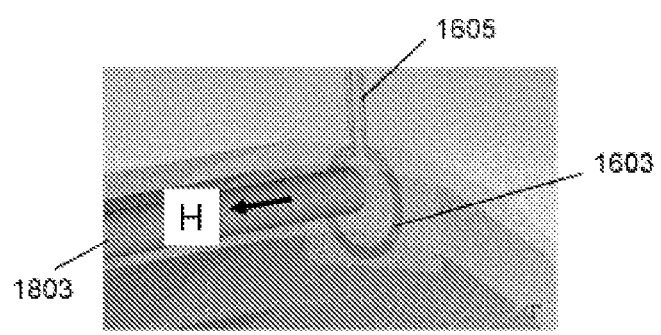
FIG. 18 shows an excitation arrangement.

FIG. 18 shows an excitation arrangement with a transmission antenna 1801 of a transmitter, which, for example, has the shape of a loop antenna illustrated in FIG. 16A. By way of example, the transmission antenna 1801 is arranged in such a way with respect to a blood vessel 1803 that a normal of the surface spanned by the frame 1603 points in the direction of the extent of the blood vessel 1803. By way of example, such an arrangement can be realized at a bend in the blood vessel 1803. As a result of this, a magnetic field component H pointing in the direction of the extent of the blood vessel 1803 is generated.

Figure 19:
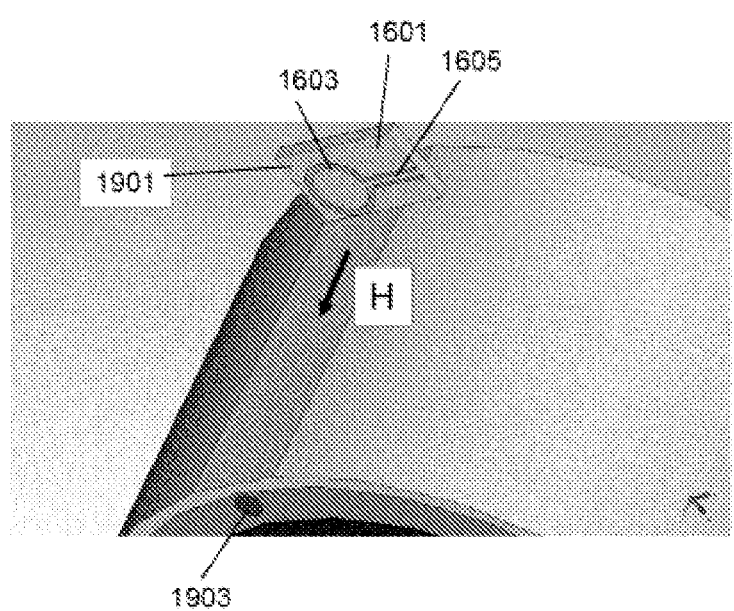
FIG. 19 shows an excitation arrangement.

FIG. 19 shows an excitation arrangement with a transmission antenna 1601, which, for example, is a loop antenna with the shape illustrated in FIG. 16A and can be arranged in a substrate 1901, for example a polymer substrate. The transmission antenna 1601 is arranged above a blood vessel 1903 in such a way that a normal of the surface spanned by the circular frame 1603 points in the direction of the extent of the blood vessel 1903. As a result of this, a magnetic field is generated with a field component H pointing in the direction of the extent of the blood vessel 1903, i.e. in the blood flow direction.

Figure 20:
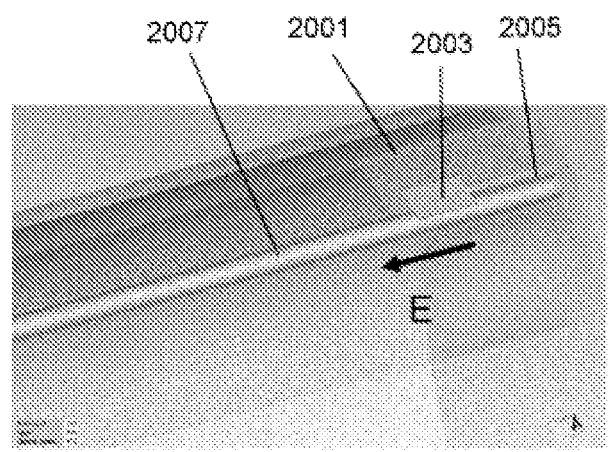
FIG. 20 shows an excitation arrangement.

FIG. 20 shows an excitation arrangement with a transmission antenna 2001, which can be a patch antenna with a patch antenna surface 2003 and supply lines 2005. The patch antenna surface 2003 is, for example, arranged above a blood vessel 2007, as a result of which an electric field is generated with an electric field component E pointing in the direction of an extent of the blood vessel 2007, i.e. in the blood flow direction.

In accordance with one embodiment, the loss detector 1107 is configured to carry out e.g. a scalar or a vector measurement or a power measurement. In order to ascertain the loss variables, a simple spectroscopic measurement can be carried out, in which the absolute value of the measurement parameter S21 is detected.

Figure 21:
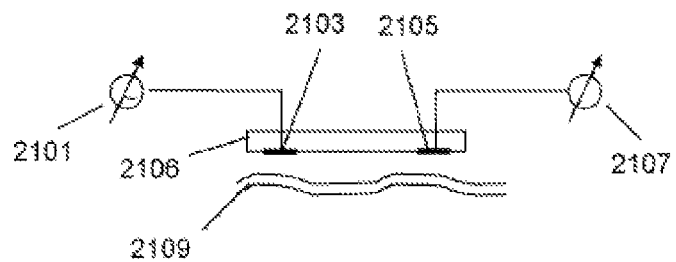
FIG. 21 shows a block diagram of a detection device.

By way of example, $|S_{21}|$ can be measured by means of the detection device illustrated in FIG. 21. The detection device comprises a transmitter with a transmission signal generator 2101, which can be a tunable oscillator. An output of the transmission signal generator 2101 is connected to a transmission antenna 2103. The detection device furthermore comprises a receiver with a reception antenna 2105, the output of which is connected to a loss detector 2107. By way of example, the loss detector can comprise a power detector. As illustrated in FIG. 21, the transmission antenna 2103 and the reception antenna 2105 are arranged above a blood vessel 2109. The transmitter can correspond to features of the transmitter 1101, the receiver can correspond to features of the receiver 1105 and the loss detector 2107 can correspond to features of the loss detector 1107.

However, the accuracy when ascertaining the loss variables, i.e. the losses in the waveguide, can be increased further by a further measurement of an absolute value of the measurement parameter S11. By way of example, the loss variables can be ascertained on the basis of the following formula:

$$P_{loss} = 1 - |S_{11}|^2 - |S_{21}|^2,$$

where $P_{loss}$ denotes the respective loss variable and where $S_{11}$ denotes the input reflection factor and $S_{21}$ denotes the forward transmission factor.

Figure 22:
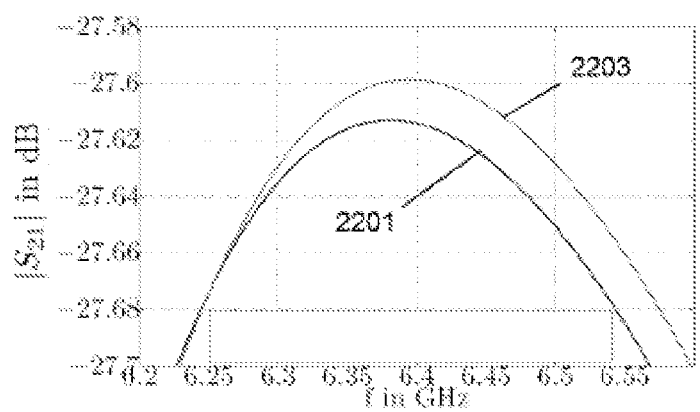
FIG. 22 shows a frequency shift of an absorption maximum.

In order to detect the blood picture parameter, for example a concentration of blood sugar, frequency shifts of the absorption lines of a water solution with sugar can, for example, be examined. By way of example, FIG. 22 shows a frequency shift of an absorption maximum 2201 at a first blood sugar concentration compared to a frequency shift of an absorption maximum 2203 at a second blood sugar concentration, which is higher than the first blood sugar concentration. Here, a transmission around 6 GHz was detected in an exemplary fashion as loss variable.

The frequency shift of the absorption maximum can be considered to be a measure for a blood picture parameter, for example for a blood sugar level. By observing frequency shifts in a number of absorptions of a water solution with sugar, the measurement reliability can be increased still further.

Figures 23, 24:
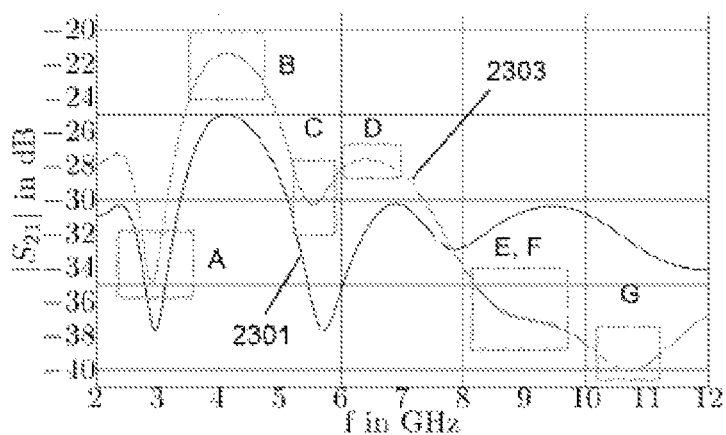
FIG. 23 shows a transmission behavior.
FIG. 24 shows frequency shifts.

FIG. 23 shows, in an exemplary fashion, a broadband transmission behavior of venous blood in a wrist. Here, the profiles 2301 and 2303 clarify different frequency positions of absorption lines at different blood sugar concentrations. In order to detect the blood picture parameter, such as, for example, the concentration of the blood sugar, it is possible, for example, to detect frequency shifts of the absorptions A, B, C, D, E, F and G in a targeted manner. Thus, it is possible, for example, to observe a shift in the direction of higher or lower frequencies depending on blood sugar level, for example in a frequency range between 2 GHz and 12 GHz, for each frequency of an absorption maximum and/or an absorption minimum.

FIG. 24 shows, in an exemplary fashion, frequency shifts of the absorptions A, B, C, D, E, F and G illustrated in FIG. 23 for a blood vessel with a diameter of 6 mm and for a blood vessel with a diameter of 3.4 mm. It is possible to identify that the absorptions for a sugar level variation can have frequency shifts in both positive and negative directions. Detecting a plurality of absorptions or absorption lines therefore makes it possible to detect a blood picture parameter, for example the blood sugar level, more accurately.

Figure 25:
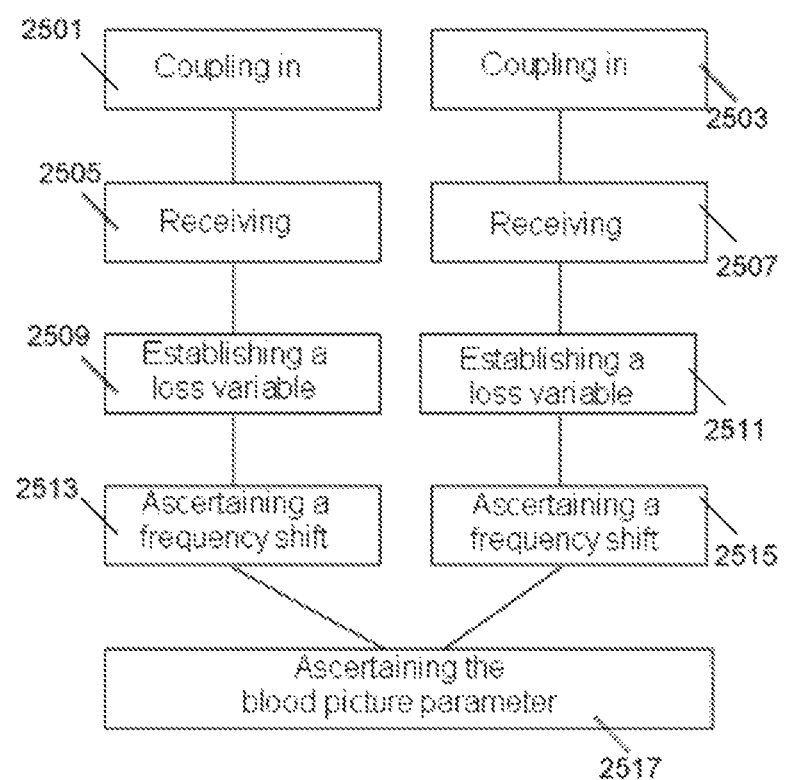
FIG. 25 shows a diagram of a method for detecting a blood picture parameter.

FIG. 25 shows a diagram of a method for detecting a blood picture parameter of blood in a blood vessel. The method comprises a first transmission signal with a first frequency being coupled 2501 into the blood vessel, a second transmission signal with a second frequency being coupled 2503 into the blood vessel, a first reception signal being received 2505 at the first frequency, a second reception signal being received 2507 at the second frequency, a first loss variable being established 2509 on the basis of the first transmission signal and the first reception signal at the first frequency, a second loss variable being established 2511 on the basis of the second transmission signal and the second reception signal at the second frequency, a first frequency shift of the first loss variable being ascertained 2513 relative to a first reference loss variable, a second frequency shift of the second loss variable being ascertained 2515 relative to a second reference loss variable and the blood picture parameter being ascertained 2517 on the basis of the first frequency shift and the second frequency shift.

By way of example, the method illustrated in FIG. 25 can be executed by the detection device illustrated in FIG. 11.

Figure 26:
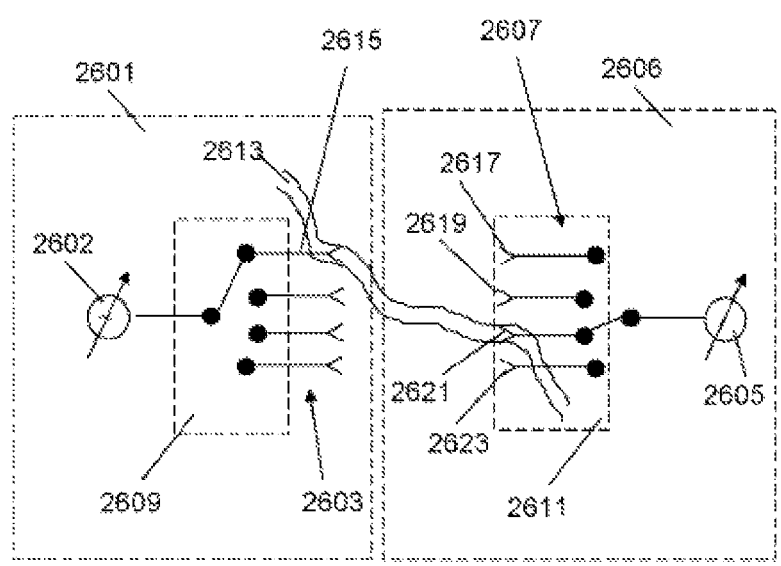
FIG. 26 shows a block diagram of a detection device.

FIG. 26 shows a detection device with a transmitter 2601, which detection device, for example, comprises a tunable oscillator 2602 and a plurality of transmission antennas 2603. The detection device furthermore comprises a loss detector 2605, which can, for example, have a power detector. Furthermore, provision is made for a receiver 2606 with a plurality of reception antennas 2607.

One output of the tunable oscillator 2602 can be connected to each antenna input, for example in succession or in any sequence, in a switchable manner, for example by means of a switching matrix 2609. Analogously to this, each output of a reception antenna of the plurality of reception antennas 2607 can be connected to the loss detector 2605 by means of a switching matrix 2611.

By way of example, the switching matrix 2611 and the switching matrix 2609 can be used to select that pair comprising a transmission antenna and a reception antenna which enables optimum coupling of a microwave signal into a blood vessel 2613 illustrated schematically in FIG. 26. The switching matrices 2609 and 2611 are used to select the antenna pairs in succession, starting with, for example, a first transmission antenna 2615 by means of which a transmission signal is emitted. The switching matrices 2609, 2611 can have switches, for example transistor switches.

On the reception side, the switching matrix 2611 is used to select the reception antennas in succession, starting with, for example, the reception antenna 2617 for receiving a corresponding reception signal, with a loss variable being detected on the basis of the transmission signal and the reception signal. In the next step, the reception antenna 2619 is for example selected, with a loss variable once again being detected by means of the loss detector on the basis of the transmission signal and a reception signal received by the reception antenna 2619. After this, for example, the reception antenna 2621 is selected, with a further loss variable being detected on the basis of the transmission signal and a reception signal. In the next step, the reception antenna 2623 is selected and a further loss variable is ascertained on the basis of the transmission signal and a reception signal received by the reception antenna 2623. In the next step, the switching matrix 2609 can, for example, select a further transmission antenna, wherein the aforementioned steps can be repeated. By a comparison of the established loss variables, the smallest loss variable, for example, is selected. In the example illustrated in FIG. 26, it is to be expected, for example, that the detection configuration with the transmission antenna 2615 and the reception antenna 2621 is afflicted with the smallest coupling-in losses because the antennas 2615, 2621 lie directly above the blood vessel and therefore enable a signal to be coupled into the blood vessel 2613 in an optimum manner. By way of example, the selected detection configuration can be used for detecting a blood picture parameter. The above-described selection steps can be carried out in any sequence. Thus, for example, all or some of the reception antennas 2607 can be tested for the transmission antenna 2615.

The transmission antennas 2603 or the reception antennas 2607 can differ in respect of their location and/or in respect of their field component which should be excited in a dominant fashion. Here, the switching matrices 2609 and 2611 ensure that the optimal excitation type, for example a loop antenna, an electric dipole antenna, a patch antenna, or excitation location can be selected for the respectively selected frequency.

By way of example, the detection device illustrated in FIG. 26 can be integrated in an inflatable armband. Between the detections of the loss variables, which can, for example, take place by measuring the control parameters, air can be allowed to escape from the armband such that the skin is aerated and no sweat is formed. A time interval between the measurements can be variable in this case. By way of example, the measurements can be carried out at intervals of 10 minutes. However, depending on requirement, more frequent measurements can be carried out, wherein the frequency of the measurements can be ascertained, for example, by the times when the meals are taken.

Since the transmission or reception antennas, which lie on the skin and can respectively be formed by an electrode plate, can slip, particularly in the pauses between the measurements, the selection of a plurality of excitation means illustrated in FIG. 26 can ensure that an excitation means which lies over the blood vessel 2613 is selected. Hence that excitation means which enables a maximum of coupling microwave energy into the blood vessel 2613 can be selected by means of the respective switching matrix 2609 and 2611.

The invention claimed is:

1. An armband suitable to contact an arm of a user, comprising:
   a detection device for detecting a blood picture parameter of blood in a blood vessel of the arm, and
   a setting device for setting a predetermined contact pressure on the arm,
   wherein:
   the detection device comprises a transmitter configured to couple at least one radiofrequency electromagnetic wave signal into the blood vessel as a waveguide and a receiver configured to receive the signal after its transmission through the blood vessel, the detection device comprises an excitation arrangement configured to generate the at least one radiofrequency electromagnetic wave signal, and the setting device is configured to set the contact pressure of the transmitter and receiver on the arm to the predetermined contact pressure.

2. The armband as claimed in claim 1, wherein the setting device is configured to set the contact pressure to the predetermined contact pressure at least during detection of the blood picture parameter by the detection device.

3. The armband as claimed in claim 1, wherein the setting device comprises a sensor apparatus for measuring a current contact pressure on the arm and a control apparatus for setting the predetermined contact pressure depending on the measured current contact pressure.

4. The armband as claimed in claim 3, wherein the sensor apparatus is arranged to contact the user's arm.

5. The armband as claimed in claim 1, wherein the armband is inflatable.

6. The armband as claimed in claim 5, wherein the setting device comprises an air pump configured to inflate the armband to set the predetermined contact pressure.

7. The armband as claimed in claim 5, wherein the setting device comprises a sensor apparatus for measuring a current contact pressure on the arm, a control apparatus for providing a control signal depending on the measured current contact pressure, and an air pump, controlled by the provided control signal, for inflating the armband.

8. The armband as claimed in claim 1, wherein the transmitter and receiver comprise electrodes.

9. The armband as claimed in claim 1, wherein the setting device is configured to distribute contact forces uniformly on the arm during detection of the blood picture parameter by the detection device.

10. The armband as claimed in claim 1, wherein the setting device is configured to provide uniform contact on the arm during detection of the blood picture parameter by the detection device.

11. The armband as claimed in claim 1, wherein the setting device is configured to keep the contact pressure constant during detection of the blood picture parameter by the detection device.

12. The armband as claimed in claim 1, further comprising a storage medium for providing information of the predetermined contact pressure.

13. The armband as claimed in claim 1, wherein the at least one blood picture parameter comprises a glucose concentration in the blood, a lactate concentration in the blood, a lactate concentration in the blood, or an oxygen concentration in the blood.

14. The armband of claim 1, wherein the transmitter includes at least one transmission antenna configured to generate the at least one radiofrequency electromagnetic wave signal such that either (i) the electric component or (ii) the magnetic component of the at least one radiofrequency electromagnetic wave signal is aligned with the direction of the blood vessel.

15. The armband of claim 14, wherein the receiver includes at least one reception antenna configured to receive a field component of the at least one radiofrequency electromagnetic wave signal.

16. The armband of claim 15, wherein the detection device includes a plurality of transmission antennas and a plurality of reception antennas.

17. A method for operating an armband, the method comprising detecting a blood picture parameter of blood in a blood vessel in the arm by coupling at least one radiofrequency electromagnetic wave signal into the blood vessel as a waveguide using an excitation arrangement including a plurality of electrodes configured to generate the at least one radiofrequency electromagnetic wave signal and receive the signal after its transmission through the blood vessel, and setting a contact pressure of the electrodes on the arm to a predetermined contact pressure on the arm.

18. A blood picture parameter detection apparatus, comprising:

an armband configured to contact an arm of a user, the armband having:
a detection device for detecting a blood picture parameter of blood in a blood vessel of the arm, and
a setting device for setting a predetermined contact pressure of the armband on the arm, wherein:
the detection device comprises electrodes configured to couple at least one radiofrequency electromagnetic wave signal into the blood vessel as a waveguide and receive the signal after its transmission through the blood vessel,
the detection device comprises an excitation arrangement configured to generate the at least one radiofrequency electromagnetic wave signal, and
the setting device is configured to set the contact pressure of the electrodes on the arm to the predetermined contact pressure.

19. A method for operating a blood picture parameter detection apparatus, the apparatus comprising an armband configured to contact an arm of a user, the armband having a detection device for detecting a blood picture parameter of blood in a blood vessel of the arm and a setting device for setting a predetermined contact pressure of the armband on the arm, the method comprising:

detecting a blood picture parameter of blood in a blood vessel in the arm by coupling at least one radiofrequency electromagnetic wave signal into the blood vessel as a waveguide using a mode excitation arrangement configured to generate the at least one radiofrequency electromagnetic wave signal and receiving the signal after its transmission through the blood vessel, and setting a predetermined contact pressure of the armband on the arm, wherein the setting device is configured to set the contact pressure of the electrodes on the arm to the predetermined contact pressure.

* * * * *